(12) United States Patent
Pierson

(10) Patent No.: US 9,410,552 B2
(45) Date of Patent: Aug. 9, 2016

(54) CURRENT SWITCH WITH AUTOMATIC CALIBRATION

(75) Inventor: David Pierson, Portland, OR (US)

(73) Assignee: Veris Industries, LLC, Tualatin, OR (US)

( * ) Notice: Subject to any disclaimer, the term of this patent is extended or adjusted under 35 U.S.C. 154(b) by 418 days.

(21) Appl. No.: 13/562,847

(22) Filed: Jul. 31, 2012

(65) Prior Publication Data

US 2013/0088213 A1 Apr. 11, 2013

Related U.S. Application Data

(60) Provisional application No. 61/543,626, filed on Oct. 5, 2011.

(51) Int. Cl.

| | |
|---|---|
| *G01R 11/32* | (2006.01) |
| *F04D 27/00* | (2006.01) |
| *H02M 1/00* | (2006.01) |
| *F04D 25/08* | (2006.01) |
| *H02P 27/04* | (2016.01) |
| *H02P 29/02* | (2016.01) |
| *G01R 1/00* | (2006.01) |
| *G01N 1/00* | (2006.01) |

(52) U.S. Cl.
CPC ............ *F04D 27/001* (2013.01); *F04D 25/08* (2013.01); *H02M 1/00* (2013.01); *H02P 27/047* (2013.01); *H02P 29/027* (2013.01); *G01N 1/00* (2013.01); *G01R 1/00* (2013.01)

(58) Field of Classification Search
CPC ............ H02M 1/00; G01R 1/00; G01N 1/00; G01N 2201/00; G01Q 10/00; H02J 1/00; H02P 1/00; H02P 2101/00; G06F 1/00; G06F 2101/00

USPC .............. 324/74, 76.19, 76.22, 76.41, 76.69, 324/674, 681, 707
See application file for complete search history.

(56) References Cited

U.S. PATENT DOCUMENTS

| | | |
|---|---|---|
| 1,100,171 A | 6/1914 | Brown |
| 1,455,263 A | 5/1923 | Oberfeil |
| 1,569,723 A | 1/1926 | Dickinson |
| 1,800,474 A | 4/1931 | Scherer |
| 1,830,541 A | 11/1931 | Harris |
| 1,871,710 A | 8/1932 | Lenehan |
| 2,059,594 A | 11/1936 | Massa, Jr. |
| 2,411,405 A | 11/1946 | Yuhas |

(Continued)

FOREIGN PATENT DOCUMENTS

| | | |
|---|---|---|
| EP | 1531334 A2 | 5/2005 |
| JP | 5083776 | 4/1993 |

OTHER PUBLICATIONS

Description of KT® 6300, 6400 Split-Core kW/kWH Transducers . . . Enercept KT®, 1 page by Hawkeye® (by Veris Industries, Inc.), at least one year prior to filing date (1997) (unavailable month).

(Continued)

*Primary Examiner* — Huy Q Phan
*Assistant Examiner* — Temilade Rhodes-Vivour
(74) *Attorney, Agent, or Firm* — Chernoff Vilhauer McClung & Stenzel, LLP

(57) ABSTRACT

A current switch that can be reset when it is not powered automatically calibrates itself when the circuit monitored by the current switch is energized.

17 Claims, 7 Drawing Sheets

(56) References Cited

U.S. PATENT DOCUMENTS

| | | | |
|---|---|---|---|
| 2,412,782 | A | 12/1946 | Palmer |
| 2,428,613 | A | 10/1947 | Boyajian |
| 2,428,784 | A | 10/1947 | Cole |
| 2,512,070 | A | 6/1950 | Nelson et al. |
| 2,663,190 | A | 12/1953 | Ilgenfritz |
| 2,746,295 | A | 5/1956 | Lubkin |
| 2,802,182 | A | 8/1957 | Godshalk et al. |
| 2,852,739 | A | 9/1958 | Hansen |
| 2,943,488 | A | 7/1960 | Strobel et al. |
| 3,190,122 | A | 6/1965 | Edwards |
| 3,243,674 | A | 3/1966 | Ebert |
| 3,287,974 | A | 11/1966 | Ciemochowski |
| 3,374,434 | A | 3/1968 | Perry |
| 3,493,760 | A | 2/1970 | Hoadley |
| 3,512,045 | A | 5/1970 | Sanger, et al. |
| 3,584,294 | A | 6/1971 | Siwko |
| 3,593,078 | A | 7/1971 | Domshy et al. |
| 3,696,288 | A | 10/1972 | Carman |
| 3,728,705 | A | 4/1973 | Atkins |
| 3,769,548 | A | 10/1973 | Pardue |
| 3,772,625 | A | 11/1973 | Raupach |
| 3,861,411 | A | 1/1975 | Mitchell et al. |
| 3,955,701 | A | 5/1976 | Fisch |
| 3,976,924 | A | 8/1976 | Vanjani |
| 4,001,647 | A | 1/1977 | Klein et al. |
| 4,001,758 | A | 1/1977 | Esper et al. |
| 4,007,401 | A | 2/1977 | Kimmel |
| 4,030,058 | A | 6/1977 | Riffe et al. |
| 4,031,462 | A * | 6/1977 | Bouvier et al. ............ 324/76.22 |
| 4,048,605 | A | 9/1977 | McCollum |
| 4,096,436 | A | 6/1978 | Cook et al. |
| 4,107,519 | A | 8/1978 | Bicek |
| D249,883 | S | 10/1978 | Collins |
| 4,124,030 | A | 11/1978 | Roberts |
| 4,151,578 | A | 4/1979 | Bell |
| 4,158,217 | A | 6/1979 | Bell |
| 4,158,810 | A | 6/1979 | Leskovar |
| 4,177,496 | A | 12/1979 | Bell et al. |
| 4,198,595 | A | 4/1980 | Milkovic |
| 4,207,604 | A | 6/1980 | Bell |
| 4,215,278 | A | 7/1980 | Barbier et al. |
| 4,227,419 | A | 10/1980 | Park |
| 4,241,237 | A | 12/1980 | Paraskevakos et al. |
| 4,249,264 | A | 2/1981 | Crochet et al. |
| 4,250,449 | A | 2/1981 | Shum |
| 4,253,336 | A | 3/1981 | Pietzuch |
| 4,258,348 | A | 3/1981 | Belfer et al. |
| 4,297,741 | A | 10/1981 | Howell |
| 4,303,979 | A * | 12/1981 | Kato et al. ...................... 702/76 |
| 4,328,903 | A | 5/1982 | Baars |
| 4,351,013 | A | 9/1982 | Matsko et al. |
| 4,354,155 | A | 10/1982 | Speidel et al. |
| 4,359,672 | A | 11/1982 | Hart |
| 4,362,580 | A | 12/1982 | Kane et al. |
| 4,363,061 | A | 12/1982 | Vaerewyck et al. |
| 4,371,814 | A | 2/1983 | Hannas |
| 4,373,392 | A | 2/1983 | Nagamoto |
| 4,384,289 | A | 5/1983 | Stillwell et al. |
| 4,386,280 | A | 5/1983 | Ricaud et al. |
| 4,388,668 | A | 6/1983 | Bell et al. |
| 4,393,714 | A | 7/1983 | Schmidt |
| 4,398,426 | A | 8/1983 | Park et al. |
| 4,408,175 | A | 10/1983 | Nelson et al. |
| 4,413,193 | A | 11/1983 | Crockett |
| 4,413,230 | A | 11/1983 | Miller |
| 4,426,673 | A | 1/1984 | Bell et al. |
| 4,432,238 | A | 2/1984 | Tward |
| 4,491,790 | A | 1/1985 | Miller |
| 4,495,463 | A | 1/1985 | Milkovic |
| 4,506,199 | A | 3/1985 | Asche |
| 4,558,310 | A | 12/1985 | McAllise |
| 4,558,595 | A | 12/1985 | Kompelien |
| 4,574,266 | A | 3/1986 | Valentine |
| 4,605,883 | A | 8/1986 | Cockroft |
| 4,621,532 | A | 11/1986 | Takagi et al. |
| 4,660,407 | A | 4/1987 | Takami et al. |
| 4,709,339 | A | 11/1987 | Fernandes |
| 4,739,229 | A | 4/1988 | Heiler, Jr. |
| 4,746,809 | A | 5/1988 | Coleman et al. |
| 4,754,365 | A | 6/1988 | Kazahaya |
| 4,757,416 | A | 7/1988 | Wilkerson |
| 4,758,962 | A | 7/1988 | Fernandes |
| 4,783,748 | A | 11/1988 | Swarztrauber et al. |
| 4,794,327 | A | 12/1988 | Fernandes |
| 4,808,910 | A | 2/1989 | Kessi |
| D301,331 | S | 5/1989 | Rhodin |
| 4,851,803 | A | 7/1989 | Hahn |
| 4,855,671 | A | 8/1989 | Fernandes |
| 4,874,904 | A | 10/1989 | DeSanti |
| 4,885,655 | A | 12/1989 | Springer et al. |
| 4,887,018 | A | 12/1989 | Libert |
| 4,890,318 | A | 12/1989 | Crane et al. |
| 4,926,105 | A | 5/1990 | Mischenko et al. |
| 4,939,451 | A | 7/1990 | Baran et al. |
| 4,944,187 | A | 7/1990 | Frick et al. |
| 4,956,588 | A | 9/1990 | Ming |
| 4,970,476 | A | 11/1990 | Kitagawa |
| 4,972,167 | A | 11/1990 | Fujioka |
| 4,991,050 | A | 2/1991 | Heberlein, Jr. et al. |
| 4,992,709 | A | 2/1991 | Griffin |
| 4,999,575 | A | 3/1991 | Germer |
| 5,003,278 | A | 3/1991 | May |
| 5,014,908 | A | 5/1991 | Cox |
| 5,039,970 | A | 8/1991 | Cox |
| 5,051,601 | A | 9/1991 | Atobe et al. |
| 5,066,904 | A | 11/1991 | Bullock |
| 5,079,510 | A | 1/1992 | Komatsu et al. |
| D323,815 | S | 2/1992 | Bouteiller |
| 5,099,193 | A | 3/1992 | Moseley et al. |
| 5,122,735 | A | 6/1992 | Porter et al. |
| 5,148,348 | A | 9/1992 | White |
| 5,162,724 | A * | 11/1992 | Katayama et al. ......... 324/76.19 |
| 5,196,784 | A | 3/1993 | Estes, Jr. |
| D335,488 | S | 5/1993 | Suzuki et al. |
| 5,223,790 | A | 6/1993 | Baran et al. |
| 5,267,122 | A | 11/1993 | Glover et al. |
| 5,296,819 | A | 3/1994 | Kuroiwa et al. |
| 5,311,138 | A | 5/1994 | Ott et al. |
| 5,317,274 | A | 5/1994 | Nakagawa et al. |
| 5,323,256 | A | 6/1994 | Banks |
| 5,337,206 | A | 8/1994 | Kadah et al. |
| 5,359,273 | A | 10/1994 | Fluckiger |
| D354,945 | S | 1/1995 | Dellavecchia et al. |
| 5,385,060 | A | 1/1995 | Wang |
| 5,391,983 | A | 2/1995 | Lusignan et al. |
| 5,397,970 | A | 3/1995 | Rowlette et al. |
| 5,410,920 | A | 5/1995 | Westwick |
| 5,426,360 | A | 6/1995 | Maraio et al. |
| 5,430,438 | A | 7/1995 | Joos et al. |
| 5,444,183 | A | 8/1995 | Gehrs et al. |
| 5,450,765 | A | 9/1995 | Stover |
| 5,467,012 | A | 11/1995 | Nystrom |
| 5,471,359 | A | 11/1995 | Simpson et al. |
| 5,473,234 | A | 12/1995 | Richardson |
| 5,502,374 | A | 3/1996 | Cota |
| 5,548,209 | A | 8/1996 | Lusignan et al. |
| 5,563,506 | A | 10/1996 | Fielden et al. |
| 5,572,073 | A | 11/1996 | Burgess et al. |
| 5,578,927 | A | 11/1996 | Perelle |
| 5,592,989 | A | 1/1997 | Lynn et al. |
| 5,596,652 | A | 1/1997 | Piatek et al. |
| 5,604,315 | A | 2/1997 | Briefer et al. |
| 5,612,499 | A | 3/1997 | Andrew et al. |
| 5,677,476 | A | 10/1997 | McCarthy et al. |
| 5,705,989 | A * | 1/1998 | Cota et al. ...................... 340/660 |
| 5,712,558 | A | 1/1998 | Saint-Cyr et al. |
| 5,753,983 | A | 5/1998 | Dickie et al. |
| 5,784,249 | A | 7/1998 | Pouliot |
| 5,808,846 | A | 9/1998 | Holce et al. |
| 5,844,138 | A | 12/1998 | Cota |
| 5,861,683 | A | 1/1999 | Engel et al. |
| 5,880,677 | A | 3/1999 | Lestician |
| 5,880,918 | A | 3/1999 | Horbelt et al. |
| 5,905,439 | A | 5/1999 | McIntyre |

(56) References Cited

U.S. PATENT DOCUMENTS

| | | |
|---|---|---|
| 5,909,087 A | 6/1999 | Bryde et al. |
| 5,920,190 A | 7/1999 | Peterson et al. |
| 5,920,191 A | 7/1999 | Maniero et al. |
| 5,922,939 A | 7/1999 | Cota |
| 5,995,911 A | 11/1999 | Hart |
| 6,005,760 A | 12/1999 | Holce et al. |
| D419,964 S | 2/2000 | Holce et al. |
| 6,020,702 A | 2/2000 | Farr |
| 6,029,524 A | 2/2000 | Klauder et al. |
| 6,044,430 A | 3/2000 | MacDonald |
| 6,046,550 A | 4/2000 | Ference et al. |
| 6,064,192 A | 5/2000 | Redmyer |
| 6,091,023 A | 7/2000 | O'Donnell |
| 6,122,972 A | 9/2000 | Crider |
| 6,124,791 A | 9/2000 | Wolf |
| D431,534 S | 10/2000 | Holce et al. |
| 6,133,709 A | 10/2000 | Puchianu |
| 6,133,723 A | 10/2000 | Feight |
| 6,137,418 A | 10/2000 | Zuercher et al. |
| 6,146,109 A | 11/2000 | Davis et al. |
| 6,219,216 B1 | 4/2001 | Holce et al. |
| 6,236,949 B1 | 5/2001 | Hart |
| 6,269,317 B1 | 7/2001 | Schachner et al. |
| 6,308,140 B1 | 10/2001 | Dowling et al. |
| 6,330,516 B1 | 12/2001 | Kammeter |
| 6,331,821 B1 | 12/2001 | Holce et al. |
| 6,344,951 B1 | 2/2002 | Sato et al. |
| 6,351,206 B1 | 2/2002 | Schweiger et al. |
| 6,373,238 B2 | 4/2002 | Lewis et al. |
| 6,380,696 B1 | 4/2002 | Sembhi et al. |
| 6,384,946 B1 | 5/2002 | Pitsch et al. |
| 6,404,166 B1 | 6/2002 | Puchianu |
| 6,414,241 B1 | 7/2002 | O'Donnell |
| D466,078 S | 11/2002 | Bowman |
| 6,496,378 B2 | 12/2002 | Holce et al. |
| 6,504,357 B1 | 1/2003 | Hemminger et al. |
| 6,504,695 B1 | 1/2003 | Holce et al. |
| 6,549,859 B1 | 4/2003 | Ward |
| 6,591,482 B1 | 7/2003 | Fleege et al. |
| D478,313 S | 8/2003 | Bowman |
| 6,615,147 B1 | 9/2003 | Jonker et al. |
| 6,636,028 B2 | 10/2003 | Lavoie et al. |
| 6,657,424 B1 | 12/2003 | Voisine et al. |
| 6,724,600 B2 | 4/2004 | Holce et al. |
| 6,737,854 B2 | 5/2004 | Bruno et al. |
| 6,756,776 B2 | 6/2004 | Perkinson et al. |
| 6,774,803 B1 | 8/2004 | Tiffin |
| 6,809,509 B2 | 10/2004 | Bruno et al. |
| 6,815,942 B2 | 11/2004 | Randall et al. |
| 6,825,771 B2 | 11/2004 | Bruno et al. |
| 6,856,515 B2 | 2/2005 | Holce et al. |
| 6,861,683 B2 | 3/2005 | Rissing et al. |
| 6,871,827 B2 | 3/2005 | Petak et al. |
| 6,888,712 B2 | 5/2005 | Holce et al. |
| 6,889,271 B1 | 5/2005 | Germer et al. |
| 6,937,003 B2 | 8/2005 | Bowman et al. |
| 6,950,292 B2 | 9/2005 | Holce et al. |
| 6,988,043 B1 | 1/2006 | Randall |
| 7,006,934 B2 | 2/2006 | Jonker et al. |
| 7,053,497 B2 | 5/2006 | Sodemann et al. |
| 7,157,899 B2 | 1/2007 | Bruno |
| 7,161,345 B2 | 1/2007 | Bruno |
| 7,193,428 B1 | 3/2007 | Baron et al. |
| 7,212,930 B2 | 5/2007 | Bruno |
| 7,221,145 B2 | 5/2007 | Bowman et al. |
| 7,230,414 B2 | 6/2007 | Bruno |
| 7,239,810 B2 | 7/2007 | Seely et al. |
| 7,310,049 B2 | 12/2007 | Bowman |
| 7,312,686 B2 | 12/2007 | Bruno |
| 7,330,022 B2 | 2/2008 | Bowman et al. |
| 7,333,345 B2 | 2/2008 | Holce et al. |
| 7,352,287 B2 | 4/2008 | Rupert |
| 7,359,809 B2 | 4/2008 | Bruno |
| 7,447,603 B2 | 11/2008 | Bruno |
| 7,855,655 B2 * | 12/2010 | Hunter et al. .............. 340/664 |
| 2004/0227503 A1 | 11/2004 | Bowman et al. |
| 2005/0240362 A1 | 10/2005 | Randall |
| 2006/0085144 A1 | 4/2006 | Slota et al. |
| 2006/0164096 A1 | 7/2006 | Kwon |
| 2007/0109708 A1 * | 5/2007 | Hussman ............... H02J 1/00 361/113 |
| 2008/0008313 A1 | 1/2008 | Fyke |
| 2008/0013351 A1 * | 1/2008 | Alexander .......... H02M 3/1582 363/123 |
| 2008/0048879 A1 | 2/2008 | Lipman |
| 2008/0150368 A1 * | 6/2008 | Gurcan ............... H02M 1/088 307/82 |
| 2009/0115400 A1 | 5/2009 | Hunter |
| 2009/0115620 A1 | 5/2009 | Hunter et al. |
| 2009/0295370 A1 | 12/2009 | Parker et al. |
| 2010/0169030 A1 * | 7/2010 | Parlos ............................ 702/58 |
| 2010/0220049 A1 * | 9/2010 | Murakami ......... H05B 33/0815 345/102 |
| 2011/0257934 A1 * | 10/2011 | Dimino ............... G01R 31/343 702/183 |
| 2011/0301464 A1 | 12/2011 | Yoo et al. |
| 2011/0313717 A1 * | 12/2011 | Lu ............................ G01P 3/48 702/147 |
| 2012/0001580 A1 * | 1/2012 | Zhang et al. ................. 318/490 |
| 2012/0300348 A1 | 11/2012 | Franks et al. |

OTHER PUBLICATIONS

Ganssie, "Interrupt Latency," Embedded.com, www.embedded.com/show Article..jhmtl?articleID=9900320, Aug. 26, 2004.

AT91M42800A Summary, "AT91 ARM Thumb Microcontrollers," Atmel, Feb. 2002.

\* cited by examiner

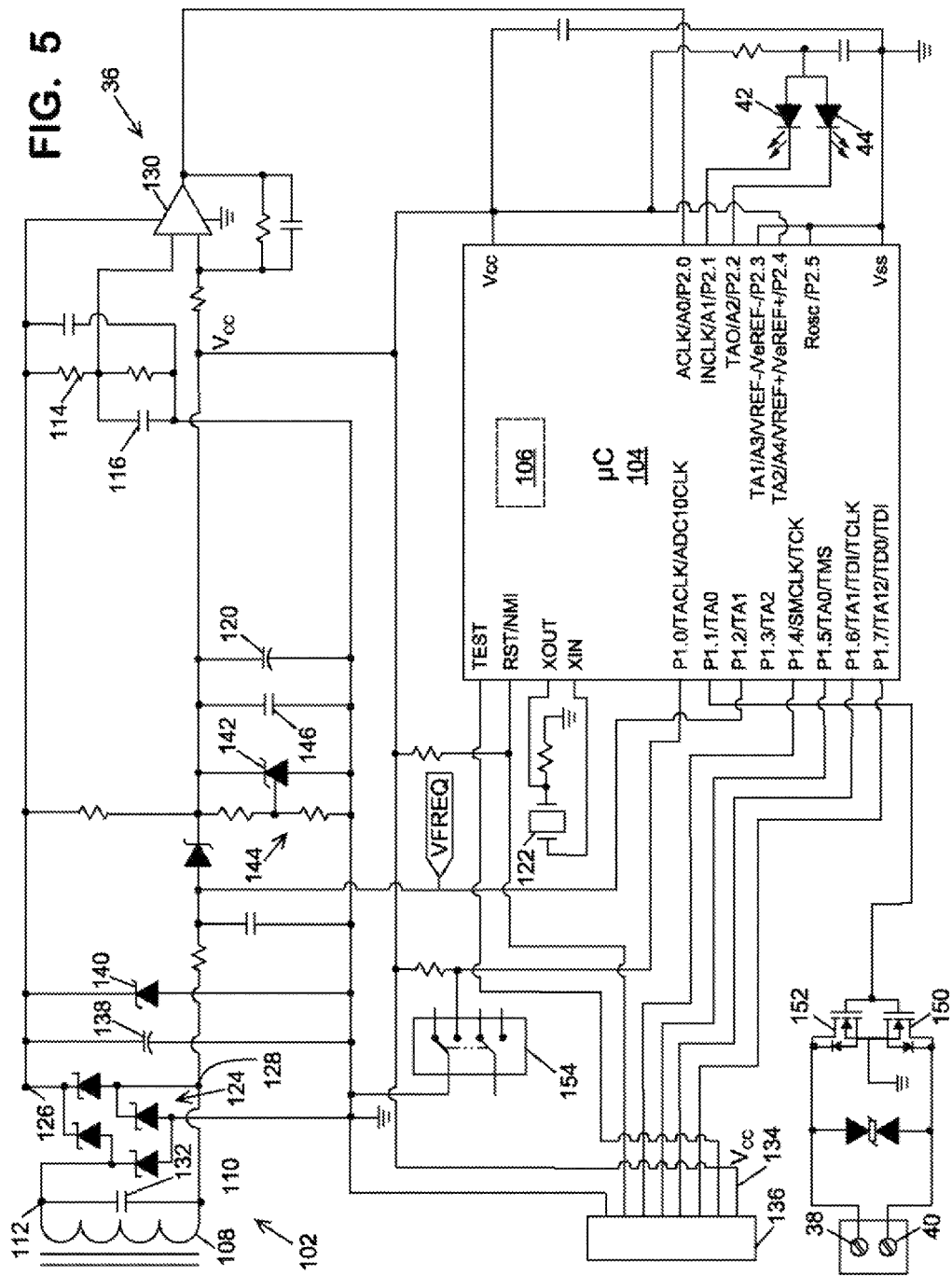

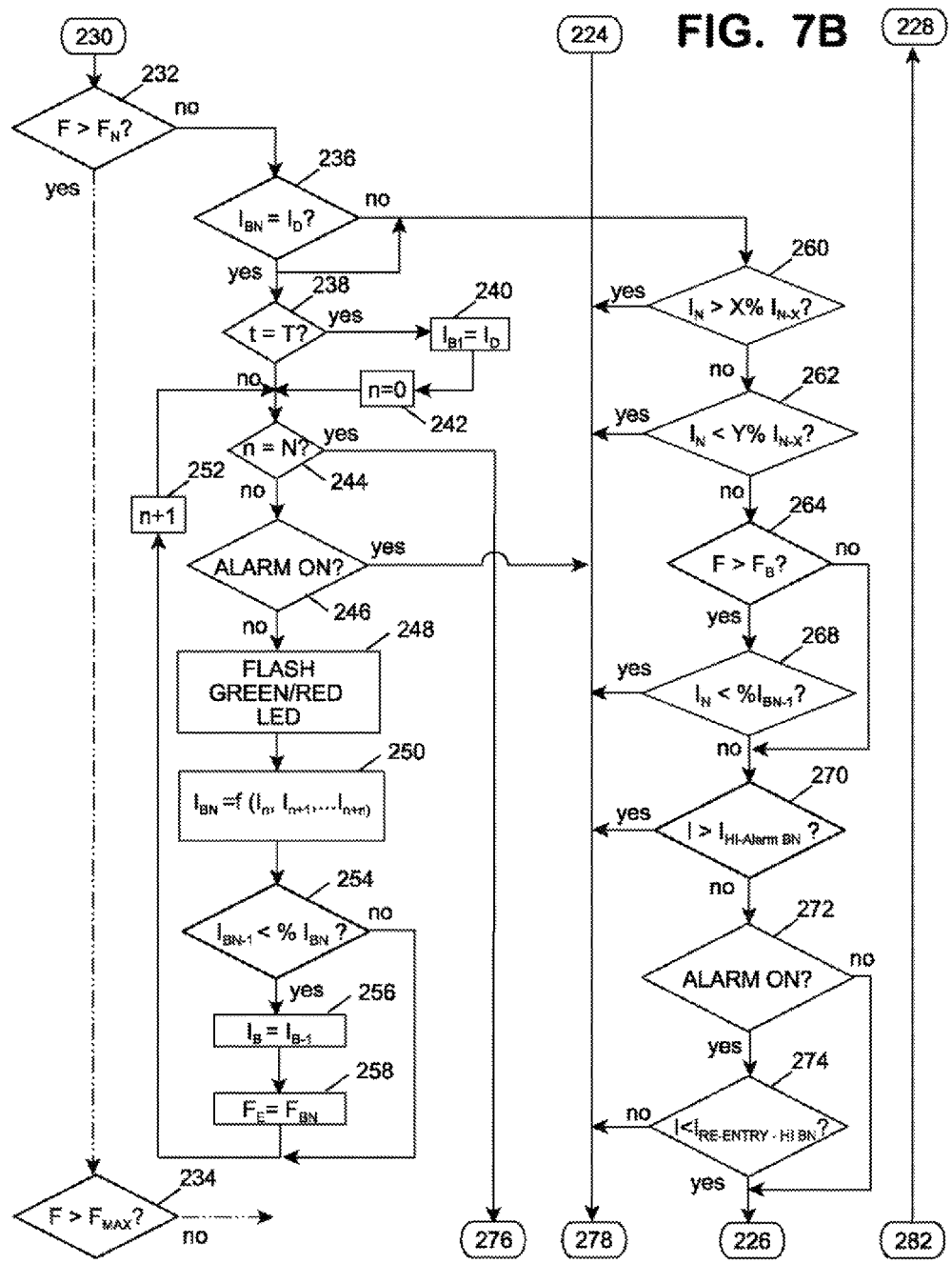

CURRENT SWITCH WITH AUTOMATIC CALIBRATION

CROSS-REFERENCE TO RELATED APPLICATIONS

This application claims the benefit of U.S. Provisional App. No. 61/543,626, filed Oct. 5, 2011.

BACKGROUND OF THE INVENTION

The present invention relates to a current switch for monitoring electric current in a conductor and enabling an alarm if the magnitude of the current is abnormal and, more particularly, to an automatically calibrated current switch.

Industrial and commercial environments utilize large numbers of electrically powered devices, such as fans, pumps and compressors. These devices are commonly driven by alternating current (AC) induction motors which are controlled by variable frequency drives (VFD). The speed of an induction motor is substantially proportional to the frequency of the input current and the basic function of the VFD is to act as a variable frequency generator to vary the speed of the motor in response to commands from a controller. The operation of these motor driven devices can be important to the protection of valuable property and successful completion of processes that may involve costly or hazardous equipment, operations or materials. The operation of these devices is commonly monitored by a current transducer that is electromagnetically coupled to a cable supplying power to the motor. The current transducer outputs a signal that is representative of the magnitude of current flowing in the cable and, if the current changes in a significant manner, the transducer transmits an alarm to the controller which may display a warning or an advisory signal on a control panel for a human operator and/or selectively enable or disable power to the device and/or other devices of a system that may be affected by a malfunction of the monitored device.

Hunter et al., U.S. Pat. No. 7,855,655 B2, discloses a current switch for monitoring a motor controlled by a VFD. To calibrate the current switch, the VFD is directed to supply a current to a motor at a frequency within each of a plurality of frequency bands. After the motor has reached steady state operation, the current switch accumulates a number of current samples, averages the magnitudes of the current samples and stores the average value as the expected motor current for that frequency band, a process that is repeated for each of the plurality of frequency bands. Thereafter, the current switch will initiate an alarm if the current differs from the average current for a frequency band by more than a predetermined percentage. While the calibration process is automatic and straight forward, it is time consuming because the VFD must be operated for approximately a minute at a frequency in each frequency band to allow the motor to reach steady state and then allow the accumulation of a number of current samples. If the installation includes a large number of current switches, the calibration process can be lengthy and there is the possibility that the installer may omit one or more frequency bands during the calibration process.

What is desired, therefore, is a current switch for monitoring the operation of a VFD controlled device which is automatically calibrated while the device is operating.

BRIEF DESCRIPTION OF THE DRAWINGS

FIG. 5 is a schematic diagram of an exemplary current switch.

FIG. 7B is continuation of the flow diagram of FIG. 7A.

DETAILED DESCRIPTION OF PREFERRED EMBODIMENTS

Figure 1:
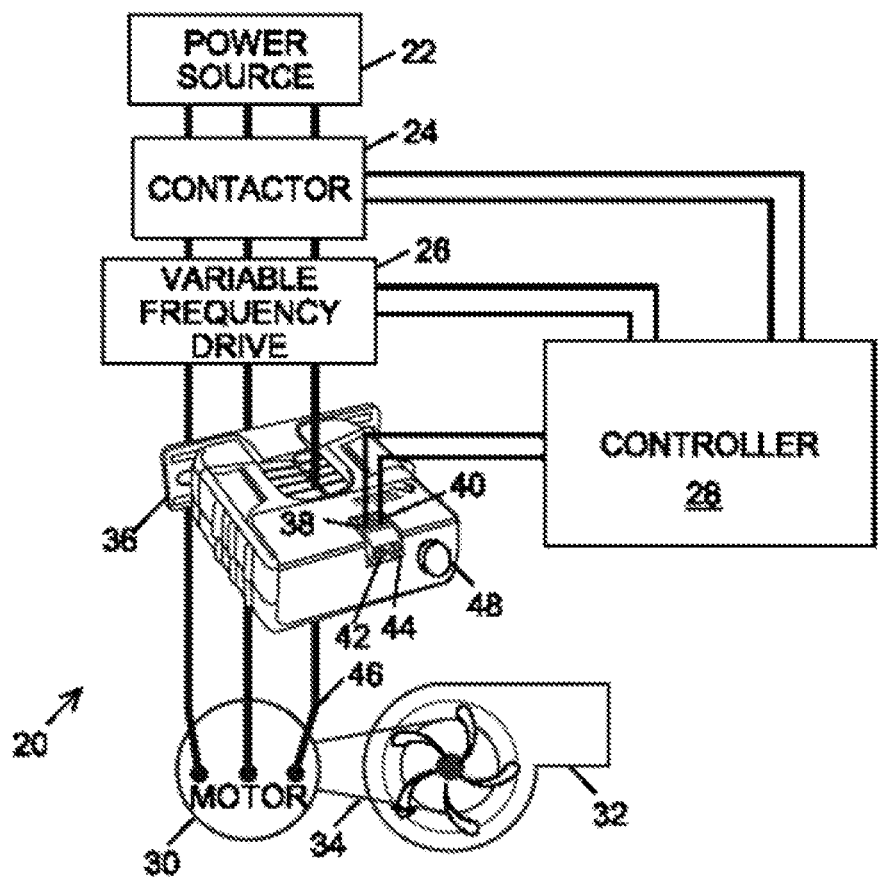
FIG. 1 is a block diagram of an electrical circuit monitored by a current switch.

Referring in detail to the drawings where similar parts are identified by like reference numerals, and, more particularly to FIG. 1, an exemplary electrically powered, mechanical system 20 includes an electrical load comprising a motor 30 that is drivingly connected by a drive belt 34 or other mechanical connection to a mechanical load 32; such as, by way of examples only, a compressor, a pump or, as illustrated, a fan. The motor is, commonly, a single-phase, alternating current (AC) induction motor or, more commonly, as illustrated, a three-phase, AC induction motor. In the exemplary system 20, a contactor 24 selectively connects a variable frequency drive (VFD) 26 to a source 22, usually a utility's power distribution grid, of single-phase or, as illustrated, three phase, AC electrical power. Typically, the VFD comprises a rectifier and a filter to convert the single-phase or three-phase alternating current supplied by the power distribution grid to direct current (DC) and an inverter under the control of a microprocessor to synthesize the DC to a single-phase or three-phase, variable frequency, AC drive signal as appropriate for the motor. The VFD acts as a variable frequency generator to vary the speed of the motor as directed by a system controller 28, which could be a human operator but is commonly a programmable logic controller (PLC) or a microprocessor based data processing system.

A current switch 36 monitors the current flow in one of the power cables 46 connecting the contactor and the motor. When the motor is running and current is flowing in the power cable, a current transducer in the current switch outputs a signal reflecting frequency and the magnitude of the current in the cable. If the magnitude of the current is within normal limits, a controller in the current switch causes terminals 38, 40 which are communicatively connected to the controller 28 to assume a NORMAL state which could be either an open or a closed conductive state. If the magnitude of the current flowing in the power cable varies significantly from a nominal current, the current switch's controller changes the connection state of the switch terminals signaling the system controller of a malfunction in the circuit monitored by the current switch.

Hunter et al., U.S. Pat. No. 7,855,655 B2, discloses a current switch for monitoring a motor controlled by a VFD. The spectrum of frequencies that can be input to the motor is divided into a plurality of frequency bands and the current switch alerts the controller if the current significantly departs from a nominal current draw for the frequency band that includes the frequency of the current being supplied to the motor. To calibrate the current switch, the VFD is directed to supply current to the motor at a frequency within one of the frequency bands. After the motor has reached steady state operation, the current switch accumulates a number of current samples, averages the magnitudes of the current samples and stores the average value as the nominal motor current for the frequencies within that frequency band. This process is repeated for each of the plurality of frequency bands. Following calibration, the current switch samples the frequency and the magnitude of the current supplied to the motor and initiates an alarm if the current differs by a predetermined percentage from the nominal current for the respective frequency band. While the acquisition of a nominal current for each frequency band is automatic, the calibration process is time consuming because the VFD must be operated at a constant frequency in each frequency band for approximately a minute to allow the motor to reach steady state and then allow accumulation of an appropriate number of current samples. If a large number of current switches are being installed, the calibration of all the current switches can be lengthy and there is the possibility that an installer may omit one or more frequency ranges during the process. The inventor concluded that the characteristics of a VFD controlled circuit and the conditions under which it would be appropriate to initiate an alarm would enable a current switch that could automatically calibrate itself while the monitored system is in operation.

Figure 2:
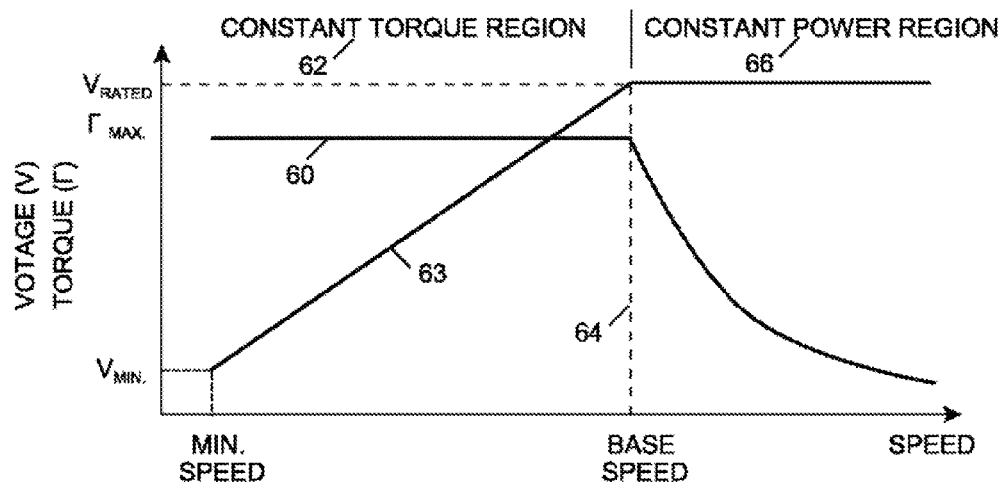
FIG. 2 is a graphical representation of the torque and voltage versus speed of an exemplary induction motor.
Figure 3:
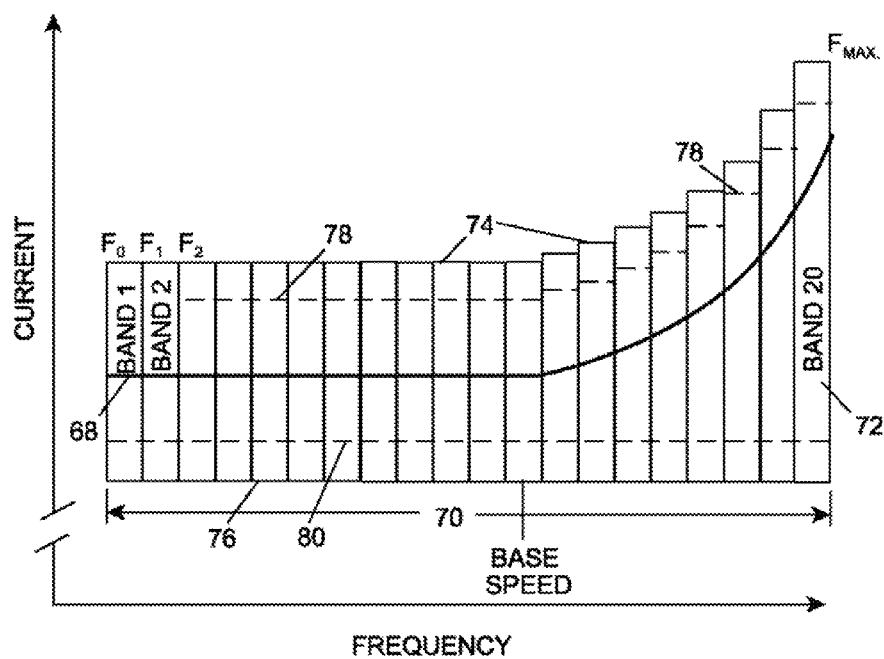
FIG. 3 is a graphical representation of the current versus frequency of an exemplary induction motor.

Referring to FIGS. 2 and 3, to regulate a motor's speed, the VFD supplies a variable frequency current to the motor. When the frequency of the drive signal is low, the equivalent impedance of an induction motor is reduced which would result in a higher current draw and an increase in magnetic flux in the motor. To keep the magnetic flux within the working range and avoid saturation of the magnetic field, the VFD varies both the supply voltage and the frequency in a constant ratio. Since the torque 60 produced by the motor is proportional to the magnetic field, the torque remains more or less constant for motor speeds up to a base speed 64 (a constant torque region 62 of the motor's operation). Induction motors can be operated at speeds up twice the base speed, but the supply voltage cannot be increased once the base speed is reached and increasing the frequency of the input current results in field weakening and reduced torque. At speeds greater than the base speed, the motor operates at substantially constant power 66 with the torque and the current 68 curves becoming nonlinear because friction and windage losses increase significantly and nonlinearly as speed increases.

Figure 4:
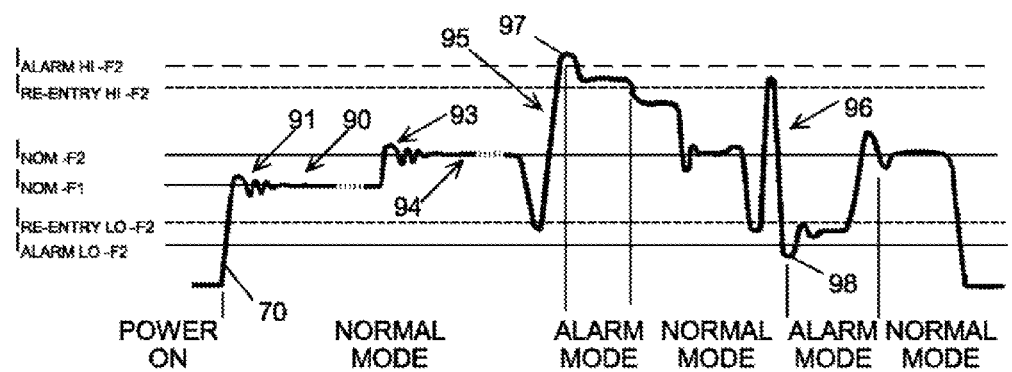
FIG. 4 is graphical representation of motor current.

Referring to also to FIG. 4, when an electric motor, drivingly connected to a mechanical load, such as a fan or a pump, is started, the current 68 in the power cable increases towards a nominal operating current for a first drive signal frequency (F1) 90 which is determined by characteristics of the motor, the mechanical load on the motor and the frequency output by the VFD. Initially, the current in the power cable may fluctuate 91 due to in-rush effects and acceleration of the mechanical load. However, the transient current excursions occurring at start up and changes in speed typically dissipate and the current draw of the motor normally settles at a relatively constant nominal current draw if the mechanical load on the motor remains constant. If the control system directs a change in the speed of the motor at speed above the base speed, the frequency of the output of the VFD will change and, following dissipation of transient currents 93, the current draw typically settles at a new nominal current ($I_{nom}$) 94 which corresponds to the new VFD output frequency (F2). A malfunction in the system is typically indicated by a significant and often sudden increase 95 or decrease 96 in the current draw of the motor. For example, an electrical short or the seizure of bearings in the motor or the mechanical load will cause a significant increase in the current draw and an abnormally high current 97 or a rapid increase in the drive signal current is an indication of a failure or a pending failure in the system. Likewise, a failure of a belt or other coupling to the mechanical load will substantially decrease the current flowing to the motor 98. The current switch 36 detects changes in the drive signal, the current flowing to the motor, and when the changes are significant enables an alarm signal to the system controller 28 which can take action, such as opening the contactor 24 to deactivate the motor and/or start or stop other portions of a larger system to avoid potential problems that might be precipitated by the failure in the monitored circuit.

Referring to FIG. 5, the automatically calibrating current switch 36 comprises, generally, a transducer 102 to detect the magnitude and frequency of the current flowing in a power cable and a data processing unit, typically a microcontroller 104 which includes a memory 106 in which data and program instructions are stored enabling the microcontroller to measure the current and frequency of the drive signal and determine whether the measured current and frequency of the drive signal are indicative of a malfunction in the monitored circuit.

Figure 6:
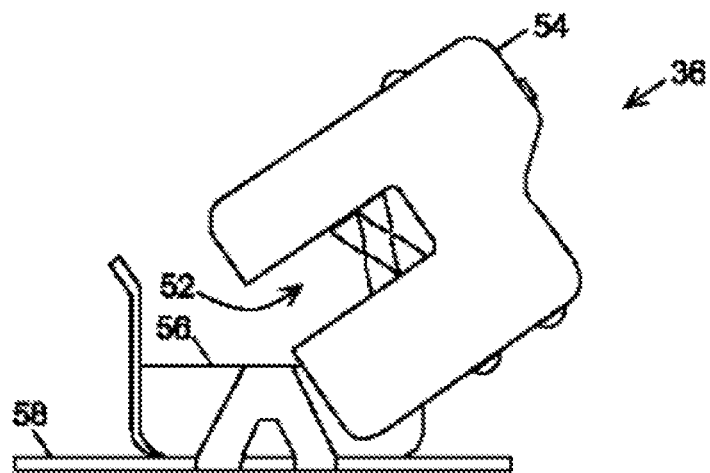
FIG. 6 is an elevation view of a current switch which includes a split core current transformer.

Although the current sensor could comprise other types of current transducers, the exemplary current transducer 36 comprises a current transformer which is, preferably, a wire wrapped toroidal core that surrounds a power cable 46 conductively connecting a power source 22 to a load 30. Referring also to FIG. 6, while the current switch may have a solid toroidal core, a split core current transformer comprising hingedly connected core portions 54, 56 simplifies installation. A current switch is typically installed in the circuit by securing a mounting bracket 58 to a structure often a portion of a motor starter enclosure. With the portions of the split core current transformer 54, 56 hinged apart the power cable can be located in the window 52. Closing the core portions 54, 56 and conductively connecting the alarm terminals 42, 44 to the system controller 28 complete the installation. The power cable serves as the primary winding of the current transformer and the wire wound on the cross-section of the toroidal core is the secondary winding 108 of the transformer. The toroidal core may be an iron core or an air core (a non-magnetically permeable material). A suitable core is disclosed in U.S. Pat. No. 5,502,374, assigned to the same assignee and incorporated herein by reference. Alternating current in the power cable produces an output voltage signal at the terminals 110, 112 of the current transformer that has a frequency corresponding to the frequency of the alternating current in the power cable and a magnitude that is related to the magnitude of the current flowing in the cable.

To determine the frequency of the alternating current in the power cable, the primary drive signal, the number of repetitions of a cyclically repeating feature of the AC signal, such as a rising edge, is counted over a specific time interval. Variable frequency drives modulate a carrier signal, with a frequency generally around 2000 Hz, to produce relatively low frequency output signals, typically 0 to 100 Hz, to operate the motor. Modulation of the carrier signal generates significant noise and other stray signals that could interfere with accurate sensing of the primary drive signal to the motor. In addition, the current transformer generates harmonics of the drive signal; for example, a 60 Hz drive signal would generate harmonics at 120 Hz, 180 Hz, 240 Hz, etc. To remove the stray signals, noise, and harmonics and to obtain a signal representative of only the primary drive signal, the AC signal at the terminals of the current transformer is filtered by a low pass filter comprising a resistor 114 and a capacitor 116. A capacitor 120 reduces ripples in the AC input to the microcontroller.

The filtered AC signal ($V_{freq}$) from the current transformer is conducted to the microcontroller 104 which includes a counter that can be triggered by a clock signal which is typically generated by an oscillator 122. The counter counts cycle distinguishing features, for example the rising edge of the AC signal until the counter receives the next clock signal. The counter is reset to zero upon receiving each clock signal and the number of rising edges detected between successive clock signals is stored. The total number of rising edges counted during a one second interval is the frequency of the alternating current in the power cable. Alternatively, both the rising and falling edges may be counted or another cycle distinguishing feature, such as zero crossing, peak amplitude, etc., might used to determine the frequency.

A rectifier 124, also connected to the terminals of the secondary winding of the current transformer, rectifies the output voltage signal from the terminals to produce a DC output signal at the rectifier's output terminals 126, 128. The DC signal is substantially proportional to the magnitude of the drive signal's current and, following differential amplification by an operational amplifier (op amp) 130, the signal is sampled by the microcontroller 104 to determine the instantaneous magnitude of the current flowing in the power cable.

A resonating capacitor 132, also connected to the output terminals of the current transformer, is selected so that it resonates at an operating frequency of the alternating current in the power cable. At frequencies near the resonate frequency of the circuit comprising the resonate capacitor and the coil of the current transformer, the resonating capacitor increases the amplitude of the voltage at the output of the current transformer. The resonance produces little effect at higher power levels but distorts the waveform sufficiently to increase the root mean square (RMS) value of the voltage signal when the drive signal current is low.

When the current in the power cable is too low for operating the microcontroller 104, power ($V_{cc}$) 134 for continued operation of the current switch is transmitted through a connector 136 from an external source (not shown).

A filter capacitor 138, connected between the output terminals of the rectifier, filters ripples in the rectifier's output signal induced by fluctuations of the current in the power cable. A diode clamp 140, in parallel with the filter capacitor, limits the magnitude of the output voltage signal from the rectifier to protect the op amp 130 from over voltage. Another diode 142 biased by a voltage divider 144 shunts excess current to ground to prevent excessive voltage at the voltage terminals of the op-amp. A capacitor 146 reduces noise in the supply voltage ($V_{cc}$) for the microcontroller.

The output of the op-amp 130 is an analog signal having an amplitude which is substantially proportional to the magnitude of the drive signal current in the power cable. The output of the op-amp is connected to a general purpose input-output pin of the microcontroller 104 which periodically samples the analog signal and converts the analog sample values to digital data (A/D) for the microcontroller's use and storage in the memory. To determine whether the operation of the monitored circuit is within normal limits, the microcontroller determines the frequency and the current of a sample of the drive signal and compares the magnitude of the current sample to stored current values appropriate for a frequency that is approximately the measured frequency of the sample.

Outputs of the microcontroller control the operation of a pair of light emitting diodes (LED) 42, 44. When the drive signal is within normal limits, a signal from the microcontroller illuminates a green LED 42 and when an alarm condition is indicated another signal from the microcontroller causes a red LED 44 to illuminate. While the current switch is calibrating, the microcontroller periodically alternates illumination of the red and green LEDs.

The terminals of the current switch 38, 40 are communicatively connected to the microcontroller by transistors 150 and 152. When a signal from the microcontroller is applied to the gates of the transistors, the terminals are conductively connected and when the gate signal is removed the connection between the terminals is opened. A conductively open or a conductively closed condition of the terminals can be selected to signal normal operation. When an alarm is activated, the conductive state of the terminals is toggled to the opposite state by a second signal output by the microcontroller to the transistors 150, 152.

The microcontroller divides the operating frequency range 70 of the drive signal into a plurality of contiguous frequency ranges or bands 72, for example twenty frequency bands, each bounded by a lower frequency, for example, $F_1$, and an upper frequency, for example, $F_2$, and determines and stores in the memory one or more alarm condition(s) applicable to each of the frequency bands. The frequency and magnitude of the drive signal are sampled substantially contemporaneously and the drive signal current is compared to the stored alarm activation conditions for the frequency band which includes the detected frequency of the drive signal. If the current in the power cable is within the predetermined limits for the respective frequency band, the system is operating normally and the green light emitting diode (LED) 42 on the current switch is illuminated. If the detected current exceeds a predetermined alarm condition, the current switch will signal an alarm state by changing the conductive status of the signaling terminals and energizing the red LED 44. If the current draw returns to an acceptable or re-entry condition, the current switch will return to the normal operating mode by returning the signaling terminals to the original conductive (or non-conductive) state, disabling the red LED and illuminating the green LED.

The inventor realized that for motor speeds below the base speed the current draw of the motor, the base current, is substantially constant and a single upper alarm activation current and a single lower alarm activation current would be appropriate for all frequency bands corresponding to speeds below the base speed. In addition, the inventor concluded that if the motor lost its load, for example, the drive belt failed, at any speed, the current draw would drop below the base current and, while a lower alarm activation current and a lower re-entry current could be determined for each frequency band corresponding to speeds above the base speed, the calibration of the current switch could be simplified by adopting a single lower alarm activation current 76 and a single lower re-entry current 80 applicable to all frequency bands up to the maximum frequency. In a preferred embodiment, the lower alarm activation current is 20% less than the nominal base drive signal current and the lower re-entry current is 15% less than the nominal base drive signal current, although other relationships of drive signal current to alarm current and re-entry current could be adopted.

An upper alarm activation current 74 and an upper re-entry current 78 are preferably a function of the nominal drive signal current 68 when the circuit is operating in the respective frequency range. In a preferred embodiment, the upper alarm activation current is 20% greater than the nominal drive signal current for a respective frequency band and the upper re-entry current is 15% greater than the nominal drive signal current when the motor is operated in the respective frequency band. Other relationships of drive signal current to alarm activation current and re-entry current could be adopted.

Figure 7A:
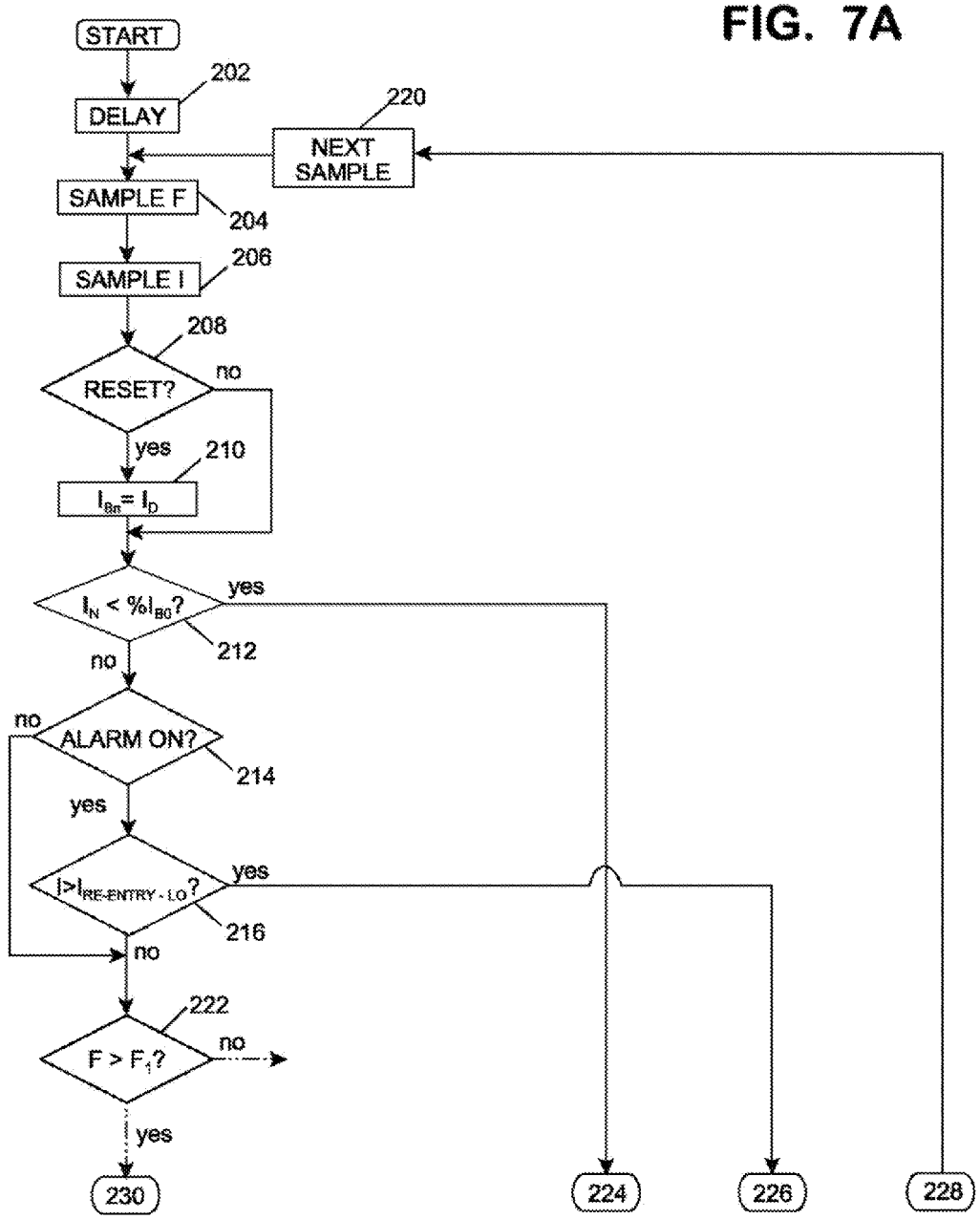
FIG. 7A is a flow diagram for operation of the current switch of FIG. 1.
Figure 7C:
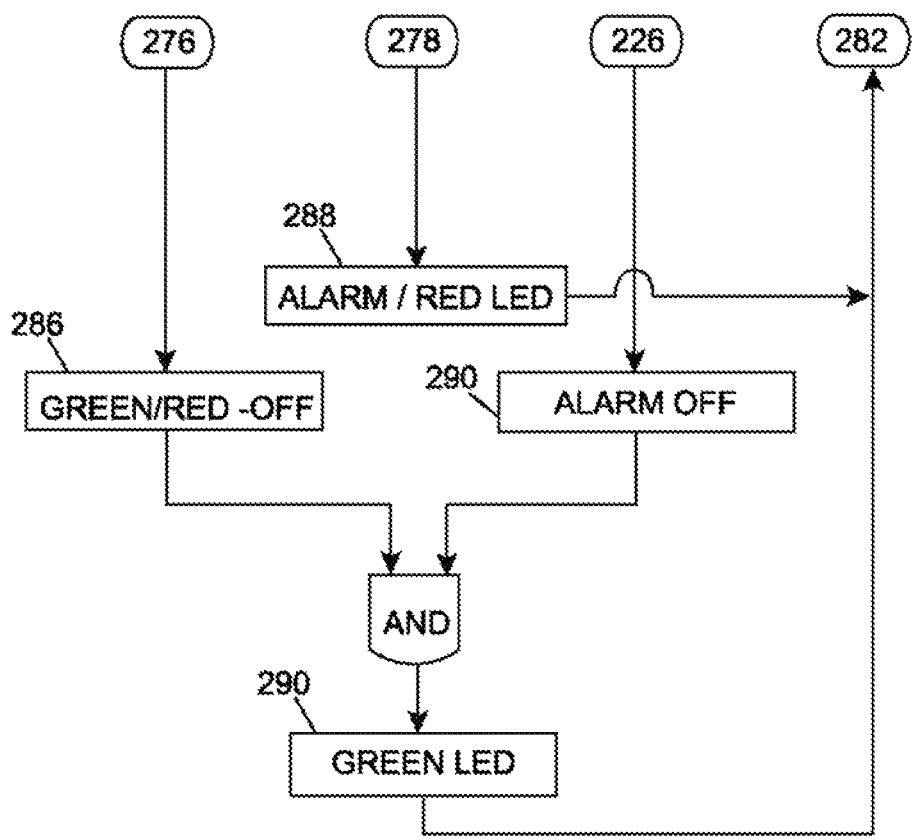
FIG. 7C is continuation of the flow diagram of FIG. 7B.

Referring to also FIGS. 7A, 7B and 7C, when power is applied to the motor by the VFD, the microcontroller 104 of the current switch 36 contemporaneously samples the frequency 204 and the current 206 of the drive signal following a delay 202 to permit the operation of the monitored circuit to stabilize and inrush currents which accompany motor start up to dissipate.

The microcontroller compares the current state of the reset switch 154 to a reset switch state that is stored in the memory of the microcontroller 208. The reset switch 154 is connected to a pin of the microcontroller 104 and the voltage at the pin indicates the current state of the switch. When a sample is taken, the microcontroller reads the current state of the reset switch and compares it to a reset switch state that was stored when a previous sample was taken to determine if the state of the switch has changed.

Current switches are commonly installed in a confined space, such as the housing of a motor starter, which often also encloses other electrical components that pose a potential risk of electrical shock when a user reaches into the enclosure to reset the current switch. The inventor concluded that the risk to a user could be reduced if the current switch could be reset while the electrical components in the enclosure were deenergized. The reset switch 154 includes an actuator, by way of examples only, a latched pushbutton 48, a rocker or a lever, that maintains the current state of the switch until the user actuates the switch a second time. If power is shut OFF to the equipment in the enclosure, including power to the current switch, before the current switch is reset, the microcontroller will read the state of the switch when power is reconnected and determine that the state has changed by comparing it to the stored data indicating the state of the switch when the power was interrupted with current state of the switch which is preserved by the switch. If the state of the reset switch changes, the microcontroller changes the values of the nominal drive signal currents 210 stored for the respective frequency bands and the current switch initiates the calibration process to establish new nominal drive current values.

The microcontroller compares the magnitude of the sample current to the base current ($I_{BO}$) 212 and, if the sample current is less than the lower alarm current (% $I_{BO}$), the microcontroller will activate the alarm 288 and then resample the drive signal 220. If the sample current exceeds the lower alarm current 214, the microcontroller determines if the alarm is activated and if it is activated determines if the current exceeds the lower re-entry current 218. If the alarm is on and the sample current exceeds the lower re-entry current, the alarm is deactivated and the red LED is extinguished 288. If the alarm is activated and the subsequent sample does not exceed the re-entry current, the alarm is maintained.

If the sample current is sufficient to avoid activating or maintaining an alarm, the microcontroller determines which of the frequency ranges 72 encompasses the frequency of the drive signal sample. The frequency of the drive signal sample is compared to a frequency limit, for example, the upper frequency, of the respective frequency bands 230, 232, 234 until a range of frequencies that includes the sample's frequency is identified. If a default value is stored for the nominal drive signal current for the frequency band that includes the sample's frequency, calibration is required for that frequency band 236.

When calibration is initiated 236, a timer is started 238 and a counter is initiated 244. Preferably, the nominal drive signal current for a frequency band is an approximation of a plurality of samples obtained during an interval of operation at frequencies within the respective frequency band. The counter determines when a predetermined number of samples have been received for calibration and the timer prevents samples obtained during momentary excursions into a frequency band from influencing the calibration of the nominal drive signal current.

If the alarm is activated 246, the alarm is maintained but if the alarm has not been activated, the green and red LEDs will be alternately illuminated 248 to signal that calibration has not been completed. The counter is incremented each time a sample is received for the calibration process 252, and if the predetermined number of samples is received before the expiration of the timer, the magnitudes of the current samples are approximated as the nominal drive signal current for the respective frequency band 250. Preferably, the approximation averages the plurality of sample currents but the approximation could determine a median value of the current samples or some other approximation might be used. If the required number of samples is not received before the timer expires 238, the default value is stored for the nominal drive signal current for the frequency band 240 and the counter is reset 242 so that calibration can again be attempted beginning with receipt of the next sample having a frequency within the respective frequency range. When a sufficient number of samples have been accumulated for calibration, the microcontroller signals cessation of the alternate illumination of the red and green LEDs 286.

When the nominal drive signal current has been determined for a frequency range 250, the microcontroller compares the nominal drive signal current to the nominal drive signal current for the next lower frequency range 254. If the nominal drive signal currents are substantially the same for the lower and higher frequency ranges, the frequency ranges lie in the constant torque portion of the motor's operation where the current draw is substantially constant over a plurality of frequency ranges. However, if the nominal drive signal current for the higher frequency range is greater than the nominal drive signal current for the lower frequency range, the upper frequency range is part of the constant power region of the motor's operation and the microcontroller stores the nominal drive signal current 256 and a frequency 258 from the lower of the two frequency ranges as, respectively, the base current and the base frequency.

One function of a VFD is the avoidance of rapid fluctuations of the motor current which would adversely affect the power factor and the electrical distribution system. Sudden changes in the drive signal current are likely the result of a malfunction, such as a short circuit or loss of a driving connection to the load. When the frequency range that includes the frequency of the drive signal sample is identified 232, the current switch compares the magnitude of the current in the sample ($I_N$) with the magnitude of the current in a sample in the same frequency range and obtained at a temporally earlier time ($I_{N-x}$) to determine if the current has either increased 260 or decreased 262 at a rate greater than a predetermined acceptable rate of change in the interval between the earlier and later samplings. If the current has increased or decreased 260, 262 at rate greater than the predetermined rate(s), the alarm is activated 288.

If the motor is operating in the constant power range, that is the drive signal sample has a frequency that is higher than the base frequency 264, the drive signal sample current is compared to the nominal drive signal current of the next lower frequency range 268, that is, the frequency range that is bounded by an upper frequency that is no greater than the lower bounding frequency of the frequency range that includes the frequency of the drive signal sample. If the drive signal current is less than the nominal drive signal current of the lower frequency band, the alarm is activated 288.

Once the calibration process has established a nominal drive signal current for a frequency band, the drive signal sample current is compared to an upper alarm activation current 270 and the alarm is activated if the sample current exceeds that limit. If the drive signal sample current does not exceed the upper alarm activation current 270 but the alarm has been activated 272, the microcontroller deactivates the alarm if the sample current is less than the upper re-entry current 274 but will maintain the alarm if the drive signal sample current is greater than the upper re-entry current for the frequency band.

If the alarm has not been activated 290 and calibration is complete 286, the green LED is illuminated indicating normal operation.

The current switch can be reset even when it is not powered and will automatically calibrate itself when it and the monitored system are energized and in operation, substantially reducing the risk, time and the possibility of error in calibrating the current switch.

The detailed description, above, sets forth numerous specific details to provide a thorough understanding of the present invention. However, those skilled in the art will appreciate that the present invention may be practiced without these specific details. In other instances, well known methods, procedures, components, and circuitry have not been described in detail to avoid obscuring the present invention.

All the references cited herein are incorporated by reference.

The terms and expressions that have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims that follow.

I claim:

1. A method of monitoring a drive signal having a variable frequency and a variable current, said method comprising the steps of:
   (a) dividing a spectrum of said variable drive signal frequencies into a plurality of contiguous frequency ranges each bounded by a lower frequency and an upper frequency;
   (b) substantially contemporaneously sampling a current and a frequency of said drive signal;
   (c) determining a first frequency range that includes said drive signal sample frequency;
   (d) activating an alarm if said drive signal sample current exceeds by a predetermined magnitude a current of a temporally prior sample of said drive signal having a frequency within said first frequency range;
   (e) activating an alarm if said temporally prior sample of said drive signal current having a frequency within said first frequency range exceeds said sample drive signal current by a predetermined magnitude;
   (f) activating an alarm if said drive signal current does not exceed a predetermined portion of a base current of said drive signal;
   (g) determining a respective nominal drive current for a plurality of said frequency ranges; and
   (h) adopting as said base current of said drive signal a current substantially equal to said respective nominal drive current for one of said frequency ranges if said nominal drive current for said one of said frequency ranges is substantially equal to a nominal drive current for at least one other frequency range.

2. The method of monitoring a drive signal of claim 1 wherein the step of determining a respective nominal drive signal current for each of said plurality of ranges of frequencies comprises the steps of:
   (a) obtaining a plurality of substantially contemporaneous samples of said drive signal current and said drive signal frequency, a frequency of each of said plurality of samples of said drive signal current being a frequency within a single frequency range;
   (b) if a predetermined number of said samples is obtained within a predetermined interval of time, approximating said plurality of current samples as said nominal drive signal current of said single frequency range.

3. The method of monitoring a drive signal of claim 2 wherein the step of approximating said plurality of current samples comprises the step of determining an average of said current samples.

4. The method of monitoring a drive signal of claim 2 wherein the step of approximating said plurality of current samples comprises the step of determining a median of said current samples.

5. A method of calibrating a current switch monitoring a drive signal having a variable frequency and a variable current, said method comprising the steps of:
   (a) said current switch dividing a spectrum of said variable drive signal frequencies into a plurality of frequency ranges each bounded by a lower frequency and an upper frequency;
   (b) if said current switch determines a state of a reset control has been changed, said current switch accumulating a predetermined number of samples of said drive signal current each having a frequency within a first frequency range; and
   (c) if said current switch determines said predetermined number of drive signal current samples is accumulated within a predetermined time interval, said current switch adopting an approximation said predetermined number of said drive signal current samples as a nominal drive current for said first frequency range.

6. The method of monitoring a drive signal of claim 5 wherein the step of approximating said predetermined number of said drive signal current samples comprises the step of determining an average of said drive signal current samples.

7. The method of monitoring a drive signal of claim 5 wherein the step of approximating said predetermined number of said drive signal current samples comprises the step of determining a median of said drive signal current samples.

8. A current switch for monitoring a drive signal having a variable frequency and a variable current, said current switch comprising:
   (a) a current transducer producing a transducer signal indicating said frequency of said drive signal and indicating a magnitude of said drive signal current;
   (b) a processing unit for executing a process according to a program instruction;
   (c) a reset control operable to indicate to said processing unit one of a first state and a second state of said reset control, said indicated reset control state preserved until said reset control is operated to indicate the other of said first state and said second state;
   (d) a memory storing a program instruction and data including a datum designating an indicated state of said reset control and a datum quantifying at least one drive signal current; and
   (e) a program instruction stored in said memory and executable by said processing unit, said program instruction causing said processing unit to change a value of said datum quantifying said at least one drive signal current if a state of said reset control presently indicated to said processing unit differs from a state of said reset control stored in said memory.

9. A current switch for monitoring a drive signal having a variable frequency and a variable current, said current switch comprising:
(a) a current transducer producing a transducer signal having a frequency related to said frequency of said drive signal and a magnitude related to said current of said drive signal;
(b) a processing unit for executing a process according to a program instruction;
(c) a memory storing a program instruction and data including a datum quantifying at least one nominal current of said drive signal; and
(d) a program instruction stored in said memory and executable by said processing unit, said program instruction causing said processing unit to:
(i) determine a frequency and a current of a sample of said drive signal from said transducer signal;
(ii) identifying a first frequency range which includes said frequency of said drive signal sample, said first frequency range one of a plurality of contiguous frequency ranges comprising a spectrum of potential frequencies for said variable frequency drive signal;
(iii) repeating steps (d)(i) and (d)(ii) to accumulate a predetermined number of samples of said drive signal current each having a frequency within said first frequency range; and
(iv) if said predetermined number of samples is accumulated within a predetermined interval of time, adopting as a nominal drive signal current for said first frequency range an approximation of said predetermined number of samples of said drive signal current.

10. The current switch of claim 9 wherein the program instruction causing the processing unit to approximate said predetermined number of samples of said drive signal current causes said processing unit to find an average of said samples of said drive signal current.

11. The current switch of claim 9 wherein the program instruction causing the processing unit to approximate said predetermined number of samples of said drive signal current causes said processing unit to find a median of said samples of said drive signal current.

12. The current switch of claim 9 further comprising a program instruction stored in said memory and executable by said processing unit to cause said processing unit to activate an alarm if said sample of said drive signal current exceeds by a predetermined magnitude a temporally prior sample of said drive signal current having a frequency within said first frequency range.

13. The current switch of claim 9 further comprising a program instruction stored in said memory and executable by said processing unit to cause said processing unit to activate an alarm if a temporally prior sample of said drive signal current having a frequency within said first frequency range exceeds said sample of said drive signal current by a predetermined magnitude.

14. The current switch of claim 9 further comprising a program instruction stored in said memory and executable by said processing unit to cause said processing unit to activate an alarm if said sample of said drive signal current does not exceed a nominal drive signal current for a second frequency range bounded by an upper frequency that does not exceed a lower frequency of said first frequency range.

15. The current switch of claim 9 further comprising a program instruction stored in said memory and executable by said processing unit to cause said processing unit to activate an alarm if said sample of said drive signal current does not exceed a predetermined portion of a base current approximating a nominal drive signal current for a second frequency range, said nominal drive signal current for said second frequency range being substantially equal to a nominal drive signal current for at least one other frequency range.

16. The current switch of claim 9 further comprising a program instruction stored in said memory and executable by said processing unit to cause said processing unit to activate an alarm if said sample drive signal current exceeds a nominal drive signal current for said first frequency range by a predetermined amount.

17. The current switch of claim 9 further comprising a reset control operable to indicate one of a first state and a second state, said reset control preserving said indicated state until operated to indicate the other of said first state and said second state; said processing unit arranged to compare said indicated state of said reset control with a stored state of said reset control and to accumulate said predetermined number of samples if said indicated state differs from said stored state.

* * * * *